United States Patent [19]
Newman

[11] Patent Number: 5,916,551
[45] Date of Patent: Jun. 29, 1999

[54] PASTEURIZED AND STERILIZED BIG GAME SCENT

[75] Inventor: Anthony Eric Newman, Shakopee, Minn.

[73] Assignee: Sequoia Management, Inc., Excelsior, Minn.

[21] Appl. No.: 08/845,711

[22] Filed: Apr. 25, 1997

Related U.S. Application Data

[62] Division of application No. 08/671,603, Jun. 28, 1996, Pat. No. 5,698,111, which is a continuation of application No. 08/349,523, Oct. 5, 1994, Pat. No. 5,565,111.

[51] Int. Cl.⁶ ............................. A01N 25/00; B01D 37/00
[52] U.S. Cl. ........................... 424/84; 210/767; 210/774; 210/806; 422/1; 422/28; 422/38; 424/537; 604/317; 53/432
[58] Field of Search ................. 424/84, 537; 422/28, 422/38, 1; 210/767, 774, 806

[56] References Cited

U.S. PATENT DOCUMENTS

| | | | |
|---|---|---|---|
| 2,959,354 | 11/1960 | Beck | 239/36 |
| 3,046,192 | 7/1962 | Bilyeu | 167/48 |
| 3,119,650 | 1/1964 | Bilyeu | 21/117 |
| 4,215,137 | 7/1980 | Dobson | 424/274 |
| 4,302,899 | 12/1981 | DeHart | 43/1 |
| 4,667,430 | 5/1987 | Ziese, Jr. | 43/1 |
| 4,768,653 | 9/1988 | Desai | 206/569 |
| 4,944,940 | 7/1990 | Christenson, II | 424/84 |
| 5,057,325 | 10/1991 | Montefiori | 424/522 |

*Primary Examiner*—Evelyn Mei Huang
*Attorney, Agent, or Firm*—Michael S. Sherrill

[57] ABSTRACT

A method of processing big game scent, such as deer lures, comprising the steps of filtering a mixture of urine and feces through a series of successively finer filters in order to remove contaminants and pathogenic bacteria from the scent without destroying or denaturing the aromatic attractants. In a second embodiment, the mixture is heated to a temperature to destroy pathogens. A third embodiment is a combination of filtering followed by heating.

6 Claims, 8 Drawing Sheets

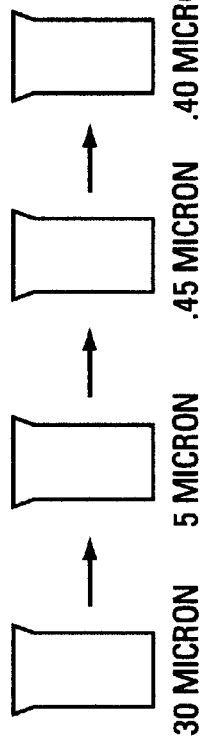
Fig. 1
FILTRATION
30 MICRON → 5 MICRON → .45 MICRON → .40 MICRON
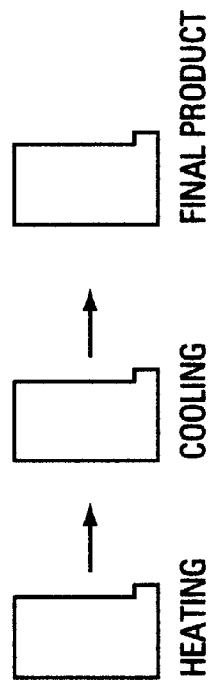
Fig. 2
HEATING COOLING
HEATING → COOLING → FINAL PRODUCT
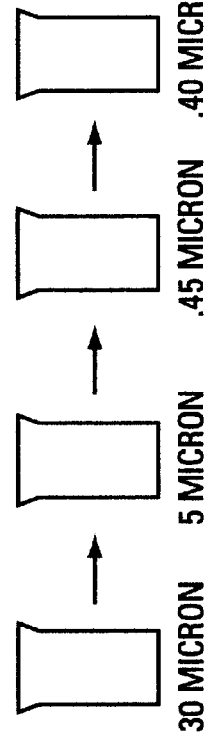
Fig. 3
FILTRATION
30 MICRON → 5 MICRON → .45 MICRON → .40 MICRON
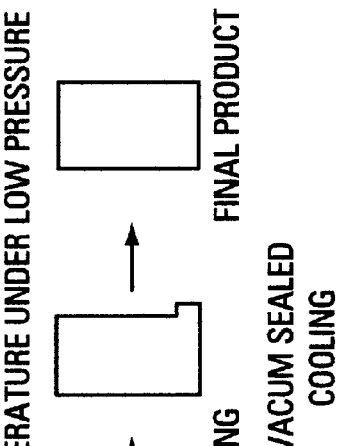
HEATING COOLING
FAST LOW-TEMPERATURE UNDER LOW PRESSURE
SEALED HEATING → VACUM SEALED COOLING → FINAL PRODUCT

UNTREATED URINE

Fig. 5a

| TIME | AREA | COMPONENT |
|---|---|---|
| 4.51 | 10.62 | METHANE, SULFONYLBIS-<br>DISULFIDE, DIMETHYL<br>OCTANE, 1,1,1,2,2,5,5,6,6-NONAFLUO |
| 4.67 | 3.97 | 1,1,2,5-D4-CYCLOPROPABENZENE |
| 5.62 | 2.41 | PRYIMIDINE,5-METHYL-<br>2-PRYIDINAMINE<br>4-PRYIDINAMINE |
| 6.64 | 51.02 | PHENOL, 4-METHYL-<br>PHENOL, 4-METHYL-<br>PHENOL, 4-METHYL- |
| 7.54 | 14.26 | PHENOL, 4-ETHYL-<br>PHENOL, 3-ETHYL-<br>PHENOL, 3-ETHYL- |
| 8.01 | 1.21 | CIS-CARVEOL<br>1,2,3,4,5-PENTAMETHYL-CYCLOPENTANE<br>PIPERIDINE,1,1'-DITHIOBIS- |
| 8.33 | 2.36 | 2-CYCLOHEXEN-1-ONE,2-METHYL-5-(1-<br>2-CYCLOHEXEN-1-ONE,2-METHYL-5-(1-<br>2-CYCLOHEXEN-1-ONE,2-METHYL-5-(1- |
| 8.64 | 0.87 | 1H-INDOLE<br>1H-INDOLE<br>1H-INDOLE |
| 9.20 | 2.14 | CYCLOHEXASILOXANE, DODECAMETHYL-<br>ACETIC ACID, [BIS[(TRIMETHYLSILYL)<br>1,1,3,3,5,5,7,7,9,9,11,11,13,13,15 |

Fig. 5b

| TIME | AREA | COMPONENT |
|------|------|-----------|
| 10.09 | 2.32 | 3-CYCLOHEXENE-1-CARBOXALDEHYDE, 1, 2,6-NAPHTHALENEDIONE, OCTAHYDRO-1, 2,6-PYRIDINEDIAMINE |
| 10.33 | 0.98 | NO MATCHES FOUND |
| 10.37 | 0.82 | 6-ACETOXY-1,3,7,7 TETRAMETHYL-2-OX 4-(1',4',4'-TRIMETHYL-2',8'-DIOXAB DIETHYL 2-(2'-METHYL-4'-OXOPENT-2- |
| 10.44 | 0.80 | 2-PROPENOIC ACID, 3-PHENYL-, TRIME PHENOL,2,6-BIS(1,1-DIMETHYLETHYL) *PHENOL,2,6-BIS(1,1-DIMETHYLETHYL) |
| 10.50 | 1.48 | OCID DTT 1TBDMS 1TMS 1,1,3,3,5,5,7,7,9,9,11,11-DODECAME PENTASILOXANE, DODECAMETHYL- |
| 11.24 | 2.19 | 1-UNDECENE 6-NITRO-O-CRESOL 1-DODECANOL |
| 11.43 | 1.67 | THIENO[3,2-C]PYRIDINE 5-OXIDE HEMI 4-MEGASTIGMEN-3, 9-DIONE PHOSHARIC ACID, 2-CHLOROETHENYL D |
| 11.97 | 0.87 | 9H-FLUORENE, 9-METHYLENE- PHENANTHRENE PHENANTHRENE |

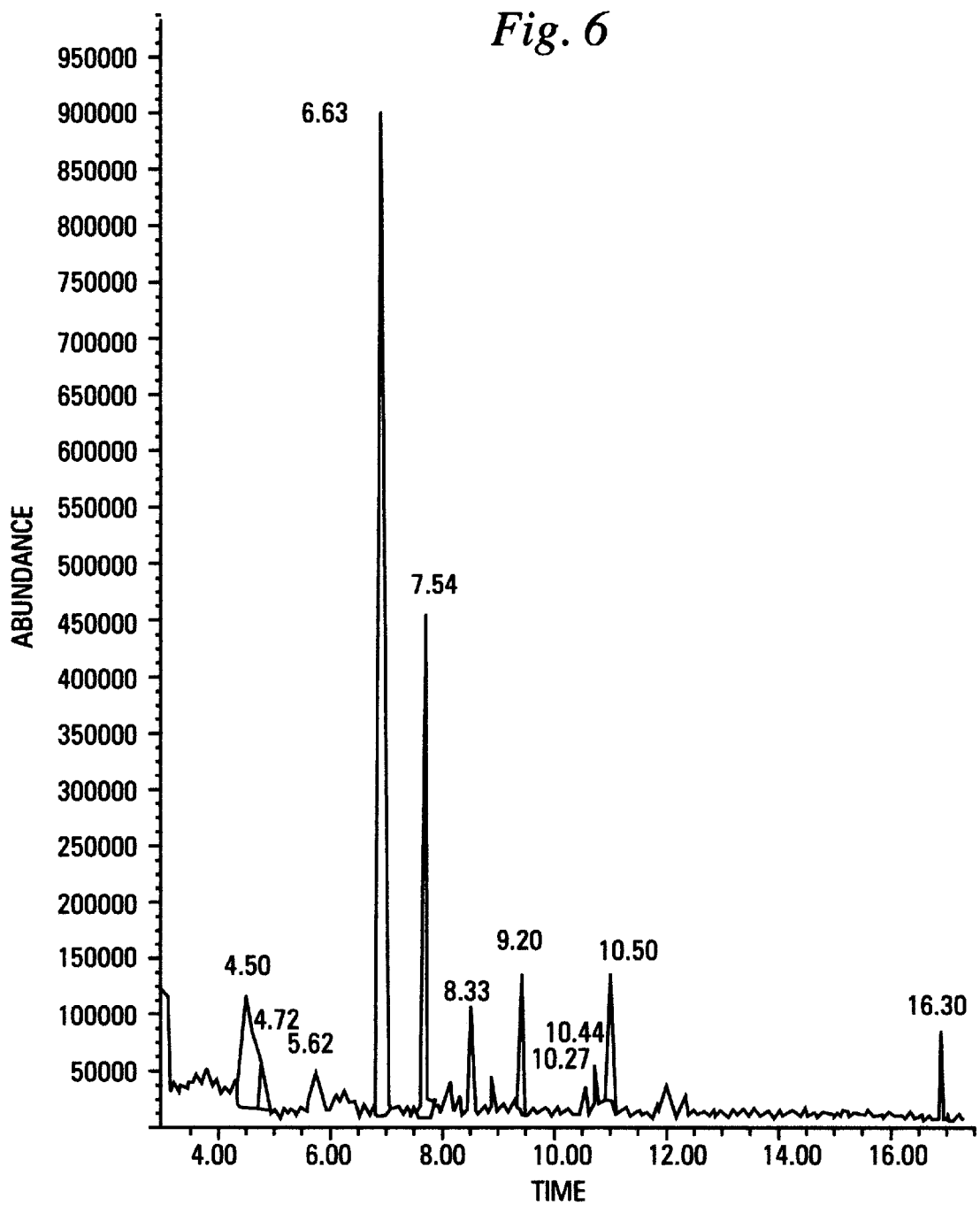

Fig. 7

| TIME | AREA% | |
|---|---|---|
| 4.51 | 12.24 | NO MATCHES FOUND |
| 4.72 | 3.38 | METHANE, SULFONYLIGIS-<br>8-AZABICYCLO[3.2.1]OCTAN-3-OL, 6-M |
| 5.62 | 0.73 | PHENOL<br>PHENOL<br>ETHNONE 1-(8HYDROXY-5-QUINOLINY |
| 6.63 | 56.47 | PHENOL, 3-METHYL-<br>PHENOL, 4-METHYL-<br>PHENOL, 4-METHYL- |
| 7.54 | 16.00 | PHENOL, 4-ETHYL-<br>PHENOL, 3-ETHYL-<br>PHENOL, 3-ETHYL- |
| 8.33 | 2.94 | 2-CYCLOHEXEN-1-ONE,2-METHYL-5-(1-<br>2-CYCLOHEXEN-1-ONE,2-METHYL-5-(1-<br>2-CYCLOHEXEN-1-ONE,2-METHYL-5-(1- |
| 9.20 | 2.72 | CYCLOHEXASILOXANE, DEDECAMETHYL-<br>1,1,3,3,5,5,7,7,9,9,11,11,13,13,15<br>METHYL 2,3-BIS(TRIMETHYLSILYLOXY)- |
| 10.27 | 1.16 | CAMPHERENONE<br>9,9-DICHLOROBICYCLO(6.1.0)NONANE<br>BICYCLO[3.3.1]NONAN-2-OL,EXO- |
| 10.44 | 1.58 | 2-PROPENOIC ACID, 3-PHENYL-, TRIME<br>PHENOL, 2,6BIS(1,1-DIMETHYLETHYL)<br>PHENOL, 2,6BIS(1,1-DIMETHYLETHYL) |
| 10.49 | 1.77 | TETRADECAMETHYLCYCLOHEPTASILOXANE<br>N-(4,4-DIDEUTERIO-4-PHENYL-BUTYL) P<br>TETRADECAMETHYLCYCLOHEPTASILOXANE |
| 16.35 | 1.01 | .GAMMA.-D4-HEXAMETHYLENE OXIDE<br>BUTANE, 3-METHYL-1-(METHYLTHIO)-<br>1-CYCLOPROPYLETHYL NITRATE |

PASTEURIZED AND STERILIZED BIG GAME SCENT

This is a divisional of U.S. patent application Ser. No. 08/671,603, filed Jun. 28, 1996, U.S. Pat. No. 5,698,111, which is a continuation of U.S. patent application Ser. No. 08/349,523, filed Dec. 5, 1994 and issued as U.S. Pat. No. 5,565,111.

BACKGROUND OF THE INVENTION

Hunting wild animals, and especially deer, is an art requiring the proper mix of intelligence, patience, endurance and the right equipment. Because deer rely heavily on their highly developed sense of smell to alert them to a multitude of factors, such as danger, food, the presence of other animals, it is necessary for the hunter to blend into the environment, without alerting the deer to his presence. It is also very helpful to provide some means to attract the animal to the hunter's vicinity.

With respect to deer, and especially the male of the species or the buck, a buck lure is often used to tempt the buck. Buck lures have application not only for deer hunters, but for photographers and other wildlife enthusiasts.

The predominant type of deer lure used today is in the form of a liquid which is generally prepared by fermenting tarsal glands of several deer in urine. The urine is usually a combination of buck, doe and fawn urine. The urine is generally collected by bringing a herd of deer into a building with grates on the floor. The deer urinate onto the grates, and the urine falls through the grates for collection.

A major problem with this method of collection of urine is, however, that the deer also defecate onto the grates and the urine thus becomes contaminated with feces. Deer feces is approximately 35% composed of bacteria (dry weight).

The bacteria which may be found in the contaminated urine include, but are not limited, to the following, all of which are pathogenic to human beings: Listeria, Shigella, *Escherichia Coli,* Salmonella, *Clostridum perfringens,* and *Giardia Lamblia.* Symptoms of infection by these organisms include: chills, fever, diarrhea, dehydration, hemorrhagic colitis, hemolytic uremic syndrome (kidney failure), brain damage, and death. The contaminated urine also may contain a variety of viruses, which are also pathogenic. Thus, the hunter who applies an untreated deer lure to the ground risks infection by any of these pathogens.

Furthermore, the presence of these organisms in the urine shortens the shelf life of the deer lure preparation because of degradation. The deer lure preparation changes to a darker or black color, which is considered to be unsellable. The store must therefore rotate its stock of deer lure preparation fairly frequently.

There is a need for a method of processing big game scent, such as deer lure preparations, which kills or removes pathogenic bacteria without destroying or denaturing the aromatic character of the lure which causes deer to be attracted to the lure.

SUMMARY OF THE INVENTION

A method of processing big game scent, such as deer lures, comprising the steps of filtering a mixture of urine and feces through a series of successively finer filters in order to remove contaminants and pathogenic bacteria from the scent without destroying or denaturing the aromatic attractants. In a second embodiment, the mixture is heated to a temperature to destroy pathogens. A third embodiment is a combination of filtering followed by heating.

A principal object and advantage of the present invention is that it kills or removes pathogenic organisms such as bacteria which may cause diseases in human beings.

A second object and advantage of the present invention is that it prolongs the shelf life of the scent by removing the organisms which cause degradation of the scent.

A third object and advantage of the present invention is that the aromatic compounds which cause deer to be attracted to the scent are not substantially destroyed or denatured by the process.

BRIEF DESCRIPTION OF THE DRAWINGS

FIG. 1 is a schematic diagram of a first method of carrying out the present invention.

FIG. 2 is a schematic diagram of a second method of carrying out the present invention.

FIG. 3 is a schematic diagram of a third method of carrying out the present invention.

FIG. 5 is table showing a chemical analysis of the gas chromatograph run of FIG. 4.

FIG. 6 is a chart of the output of a gas chromatograph run on a sample of deer urine treated vacuum-sealed heating and cooling.

FIG. 7 is table showing a chemical analysis of the gas chromatograph run of FIG. 6.

FIG. 8 is a table showing the results of bacterial cultures performed on urine treated by the methods of this invention.

DETAILED DESCRIPTION OF THE PREFERRED EMBODIMENTS

Figure 4:
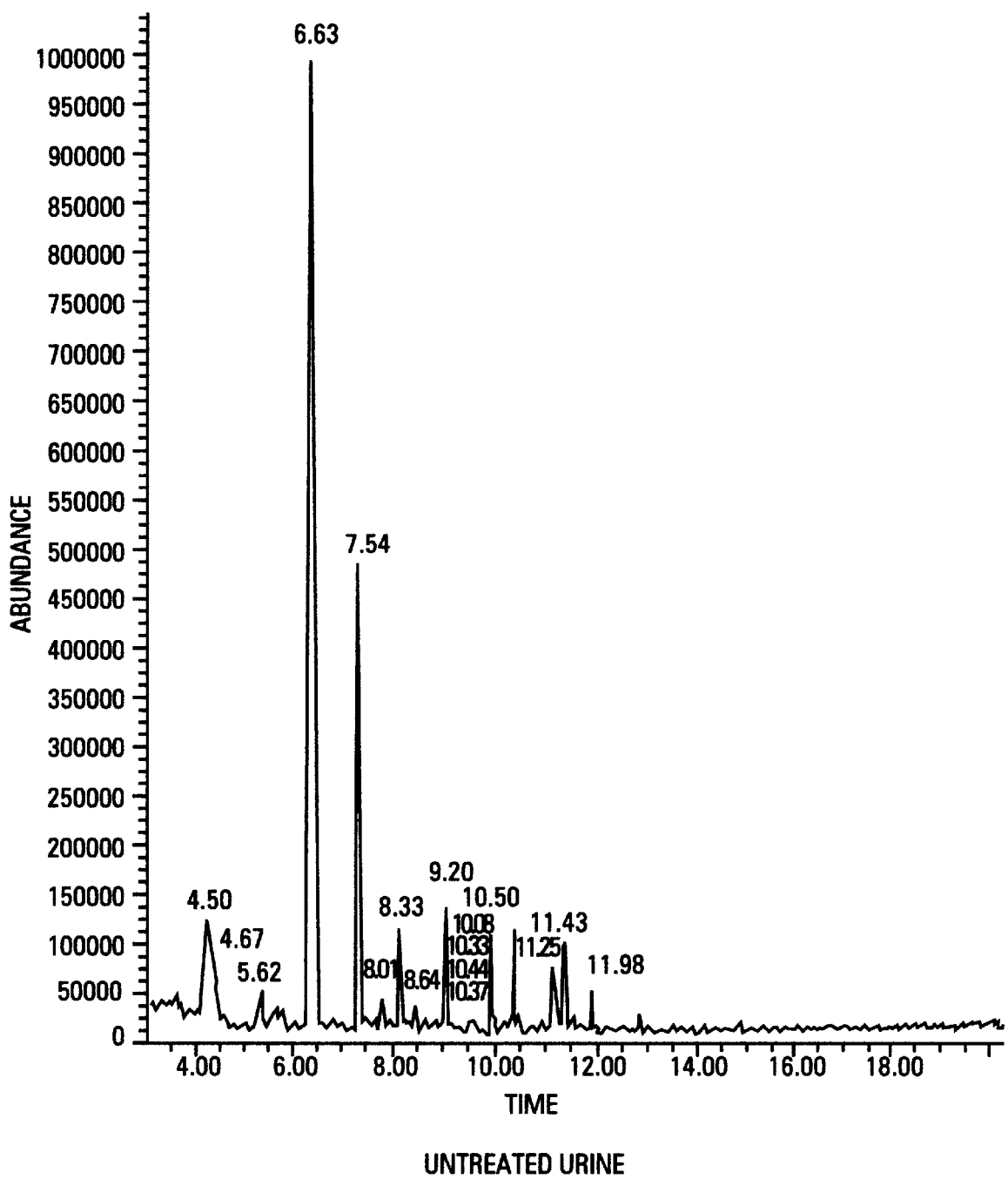
FIG. 4 is a chart of the output of a gas chromatograph run on a sample of untreated deer urine.

FIG. 1 shows the steps involved in a first method of carrying out the present invention. In the first step (not shown), urine is collected from an animal. Urine is generally collected by bringing the animal into an enclosure with a floor consisting of a grate with openings. As the animal urinates, urine falls through the grate and is collected in containers placed under the grate, as is well known in the art. As the animal defecates, feces also falls through the grate openings and becomes mixed with the urine. The fecal matter must be removed from the urine, because feces contains approximately 35% (dry weight) of bacteria.

The first method of carrying out the present invention involves filtering the feces/urine mixture through a series of successively finer filters.

The first filter in the series must be coarse enough to remove particulate fecal matter (greater than 30 microns) without clogging. If too coarse a filter is used, the fecal matter will not be removed. If too fine a filter is used, the fecal matter will quickly clog the filter and inhibit filtration. In the preferred embodiment, the first filter comprises a filter with pores of 30 microns in diameter. The urine is filtered through the first filter to produce a first filtrate.

Next, a second coarse filter is employed to remove particulate matter not removed by the first filter. In the preferred embodiment, a filter with pores 5 microns in diameter is used. The first filtrate is filtered through the second filter to produce a second filtrate.

In the third step, a filter with pores small enough to prevent the passage of bacteria is used. In the preferred embodiment, the third filter has pores 0.45 microns in diameter. The second filtrate is filtered through the third filter to produce a third filtrate.

In the fourth step, another filter with smaller pores is used to remove any bacteria passed through the third filter. In the preferred embodiment a filter with pores 0.40 microns in diameter is used. The third filtrate is filtered through the fourth filter, producing a fourth filtrate.

In contrast to an untreated specimen of deer urine/feces, which may contain millions of CFU/ml., FIG. 8 shows that the first method has removed essentially all bacteria from the sample.

FIG. 8 shows the results of a bacterial culture run on the fourth filtrate. Sample 1 was filtered according to the first method described above, put into an unsanitized bottle, and sampled for bacteria by known standard methods. Sample 2 was treated identically, except that a musk scent was added to the urine. FIG. 8 shows that Sample 1 and Sample 2 contain, respectively, 1400 and 10 colony-forming units/ml. (CFU/ml.).

FIG. 2 shows the steps involved in a second method of carrying out the present invention. The mixture of feces in urine is collected as described above. Then the mixture is placed in a container. The container may be vacuum-sealed, or the bottles used for selling the final product may be used.

After placing the mixture in the container, the container and the mixture therein are heated to a temperature sufficient to kill pathogenic organisms such as bacteria and viruses. The critical temperature for killing such organisms is 161 degrees Fahrenheit. However, use of a temperature significantly higher than the critical temperature may cause the aromatic attractant compounds in the scent to denature or be destroyed.

In one preferred embodiment, the container is vacuum-sealed and the container and the mixture are heated to a temperature of 163 degrees Fahrenheit and held at that temperature for 45 seconds. It has been found that this temperature and time period kill all bacteria without significantly altering the aromatic attractant compounds in the scent, as will be discussed below.

After the heating step, the container and the mixture are cooled to approximately room temperature. In the preferred embodiment, the cooling step is carried out by circulating cold water around the container for approximately 10 minutes.

In another embodiment, the container comprises the bottle that will be used in selling the final product, and is not vacuum-sealed. Without vacuum-sealing, the method is modified so that the heating step comprises heating the container and mixture to 145 degrees Fahrenheit for 30 minutes. It has been found that vacuum-sealed heating and cooling are not necessary at this lower temperature in order to avoid altering the aromatic attractant compounds in the scent.

FIG. 4 shows the results of a gas chromatography analysis of a sample of untreated deer urine, and FIG. 5 is a table showing the chemical composition found by gas chromatography. FIGS. 6 and 7 are corresponding figures showing the results of a gas chromatography run on a sample of deer urine treated by vacuum-sealed heating and cooling.

It will be clear to the observer that FIG. 6 and FIG. 4 are very similar. That is, the major chemical compounds of the urine, responsible for the scent are left untouched by the vacuum-sealed heating and cooling. FIGS. 5 and 7 confirm that the major chemical compounds of the urine responsible for the scent are left untouched by the method.

Figure 9:
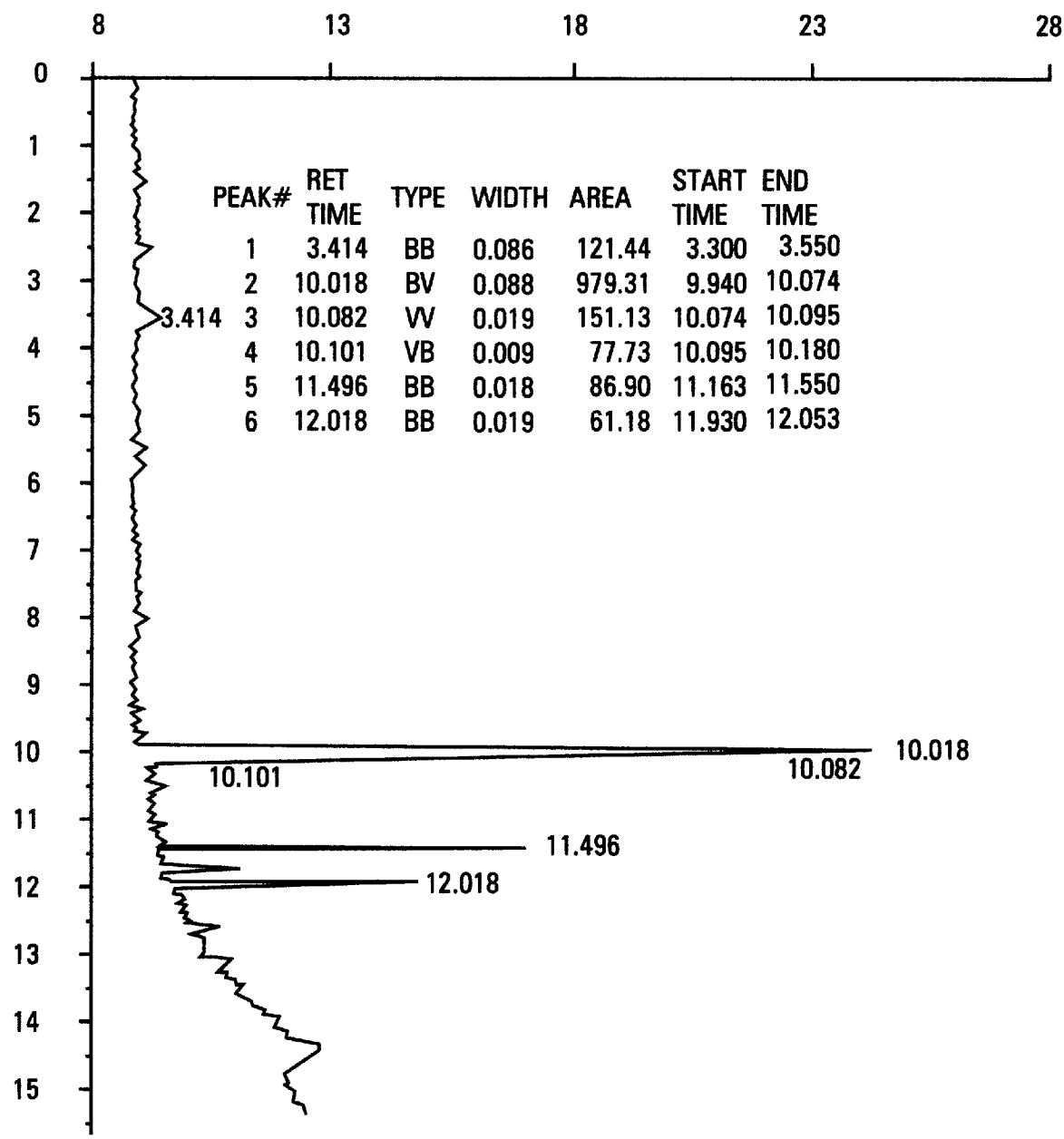
FIG. 9 is a chart of the output of a head-space gas chromatograph run on a sample of untreated deer urine.
Figure 10:
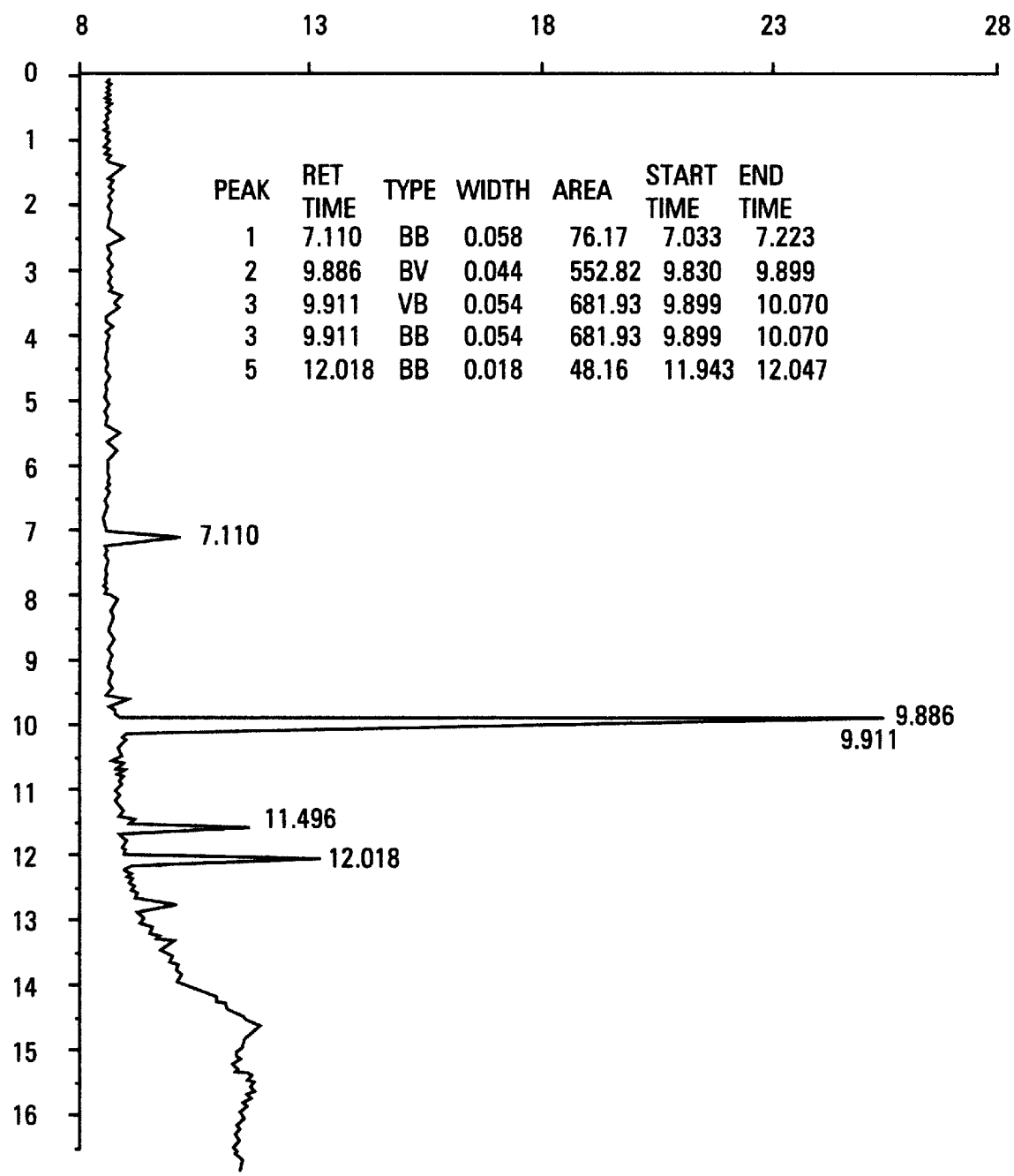
FIG. 10 is a chart of the output of a head-space gas chromatograph run on a sample of deer urine treated by vacuum-sealed heating and cooling.

To confirm that the major volatile compounds of the urine are not removed by the heating and cooling of the urine, a head-space gas chromatography run was performed. In head-space gas chromatography, a sample of the air above the urine in a sealed container is removed and analyzed. This "head-space" air will contain mainly volatile compounds. FIG. 9 shows a head-space gas chromatography run on untreated urine. FIG. 10 shows a head-space gas chromatography run on urine treated by heating and cooling as described above. There is very little difference in the two runs, indicating that the volatile compounds have not been destroyed or denatured by the heating and cooling process.

To confirm that essentially all bacteria were killed by heating and cooling as described, a bacteria culture was performed on the product after heating and cooling as described above. FIG. 8, Sample 3, shows the results. It will be seen that the treated sample contains less than 10 CFU/ml., showing that essentially all bacteria have been removed.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. An animal scent packaged for retail sale obtained by the process comprising (i) collecting animal urine optionally contaminated with animal fecal matter, (ii) sieving the animal urine to remove particulates from the urine, and (iii) pasteurizing the animal urine at a temperature effective to kill bacteria without substantially denaturing or destroying aromatic attractant compounds in the urine.

2. An animal scent packaged for retail sale obtained by the process comprising (i) collecting animal urine contaminated with animal fecal matter, (ii) sieving the animal urine to remove particulates from the urine, and (iii) filtering the animal urine so as to remove bacteria without removing aromatic attractant compounds in the urine.

3. The animal scent of claim 1 wherein the pasteurized big game animal urine comprises a pasteurized mixture of big game animal urine and big game fecal matter.

4. The animal scent of claim 2 wherein the filtration sterilized big game animal urine comprises a filtration sterilized mixture of big game animal urine and big game fecal matter.

5. The animal scent of claim 1 wherein the pasteurized big game animal urine is packaged for retail sale as a hunting scent.

6. The animal scent of claim 2 wherein the filtration sterilized big game animal urine is packaged for retail sale as a hunting scent.

* * * * *